US012472380B2

(12) United States Patent
Weil

(10) Patent No.: US 12,472,380 B2
(45) Date of Patent: Nov. 18, 2025

(54) GRADIENT OPTIMIZED RADIAL TREATMENT (GORT)

(71) Applicant: Michael D. Weil, Half Moon Bay, CA (US)

(72) Inventor: Michael D. Weil, Half Moon Bay, CA (US)

( * ) Notice: Subject to any disclaimer, the term of this patent is extended or adjusted under 35 U.S.C. 154(b) by 258 days.

(21) Appl. No.: 18/099,668

(22) Filed: Jan. 20, 2023

(65) Prior Publication Data

US 2024/0245931 A1 Jul. 25, 2024

(51) Int. Cl.
*A61N 5/10* (2006.01)
*A61N 5/00* (2006.01)

(52) U.S. Cl.
CPC ......... *A61N 5/1039* (2013.01); *A61N 5/1067* (2013.01); *A61N 5/1084* (2013.01); *A61N 2005/005* (2013.01)

(58) Field of Classification Search
CPC .............. A61N 2005/1091; A61N 5/10; A61N 5/1049; A61N 5/1067; A61N 5/1081; A61N 5/1083; A61N 5/1084; A61N 5/103
See application file for complete search history.

(56) References Cited

U.S. PATENT DOCUMENTS 8,050,384 B2 * 11/2011 Carol .................. A61N 5/1039 378/65

* cited by examiner

*Primary Examiner* — David J Makiya
*Assistant Examiner* — Miya Downing

(57) ABSTRACT

The present invention relates to the field of medical therapy of lesions detrimental to a body. The system is capable of treatment with a non-invasive, ionizing kV energy radiation source. Locally focused energy can be used to definitively treat, or as an adjuvant to enhance immune modulators, to eliminate tumors. Distributed external beam entry points produce a significant advantageous dose profile at depth as intersecting beams accumulate in a narrow focus to treat a selected volume. Targeted disease may have enhanced sensitivity to the radiation by taking up an ionizing-radiation, treatment-localizing agent. This increases the effectiveness of an energy dose in the lesion. The pattern of beam output is effectively directed towards a desired location and kV x-rays traveling towards undesired locations, such as healthy tissue, are quenched. Targeting a lesion within the body with volumetrically discrete energy dose deposition can beneficially impact harmful lesions. Aiming the beam at a pathologic target is done while moving an x-ray source mechanically around a patient to distribute surface dose. The purpose of the focused energy deposition is to destroy and disable pathologic physiology, such as malignant masses. More specifically this invention relates to a system, which optimizes delivery of ionizing kV beams to a lesion alone or one containing treatment-localizing agents in higher concentration than the surrounding normal tissues. Thereby an optimal delivery of ionizing radiation becomes more destructive to a mass of abnormal cells upon interaction with the targeted site.

6 Claims, 7 Drawing Sheets

(Long SSD - Head)

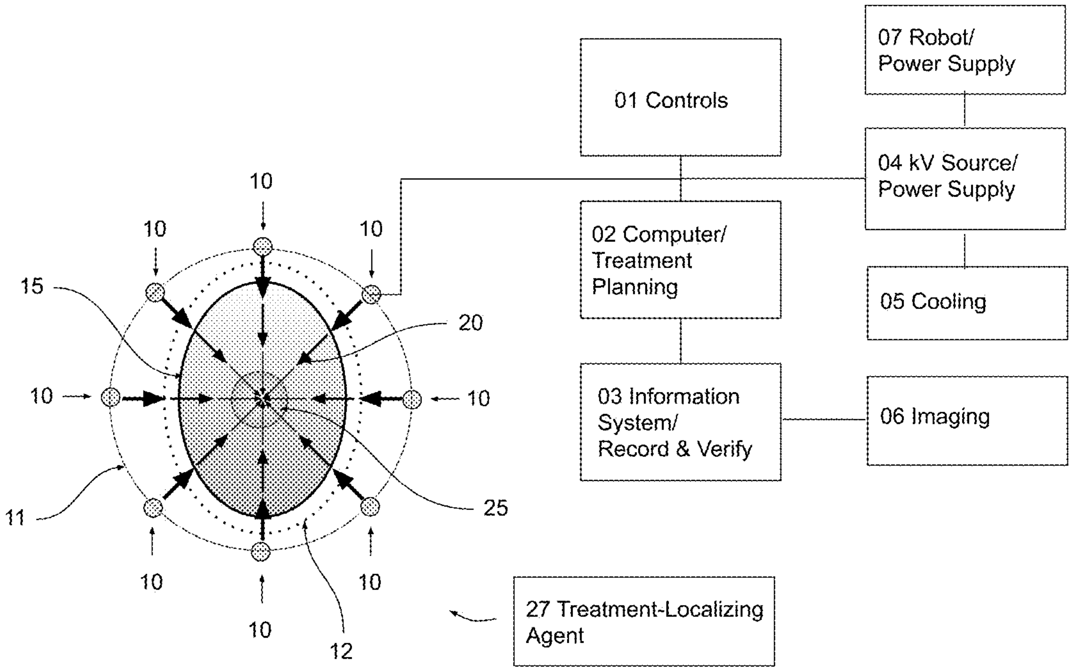
FIG. 1 (Long SSD - Head)

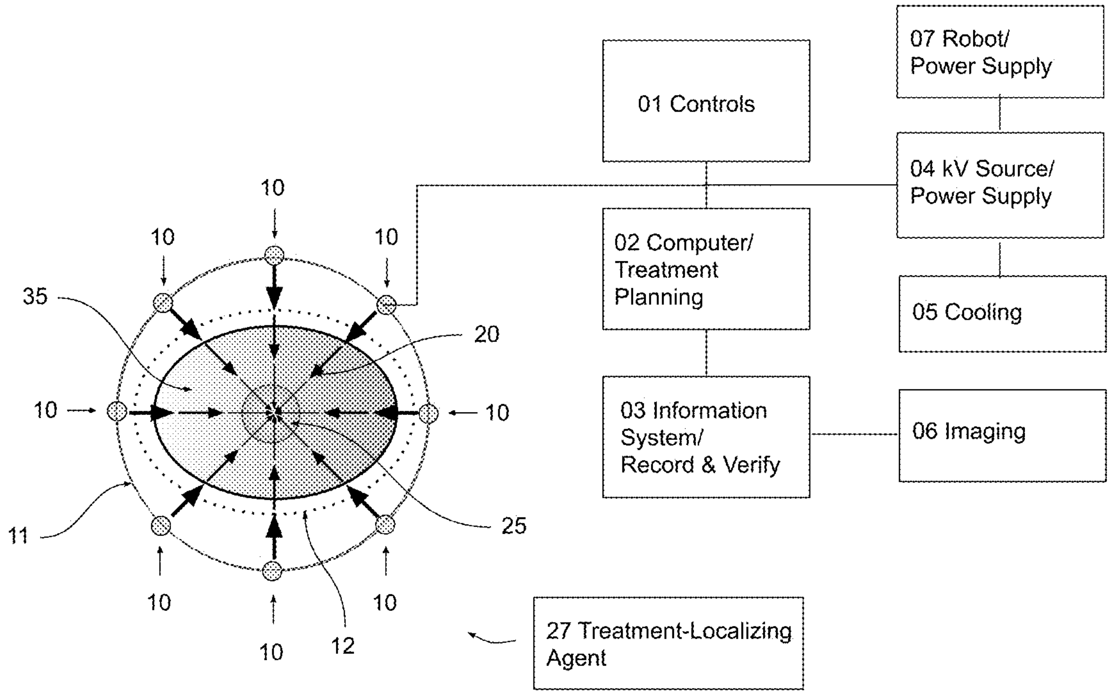
FIG. 2 (Long SSD - Body)

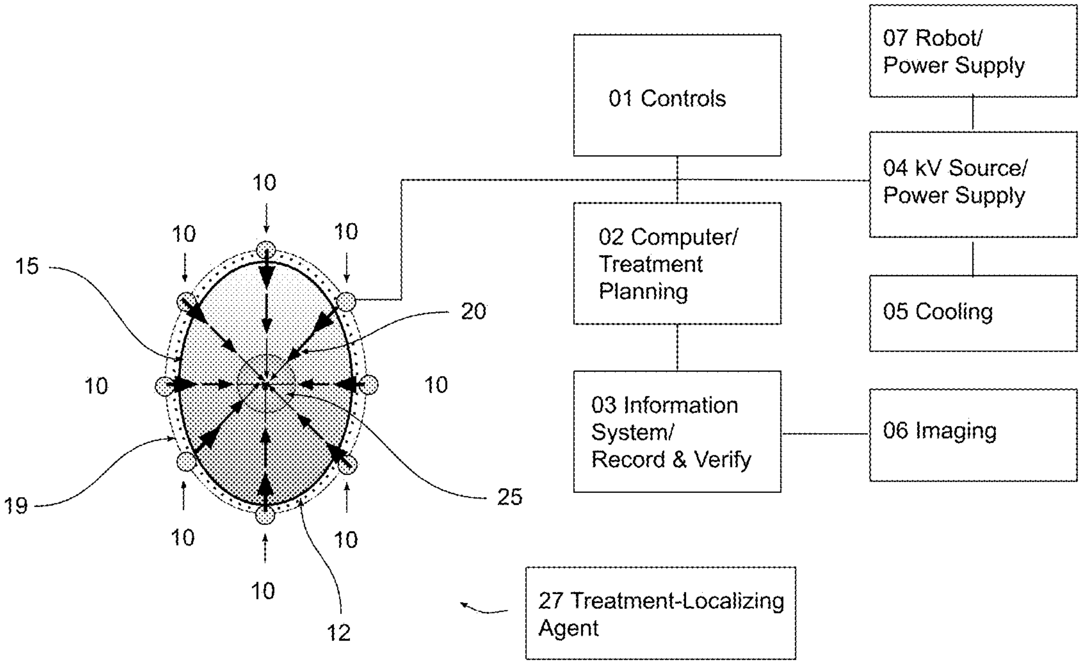
FIG. 3 (Short SSD - Head)

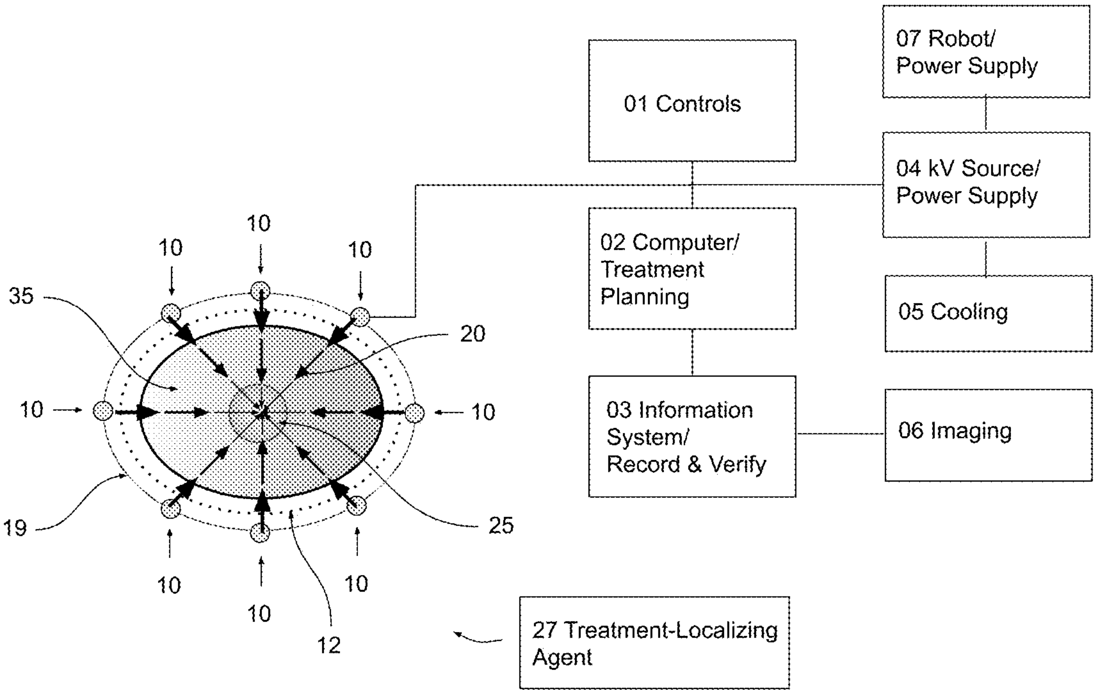
FIG. 4 (Short SSD - Body)

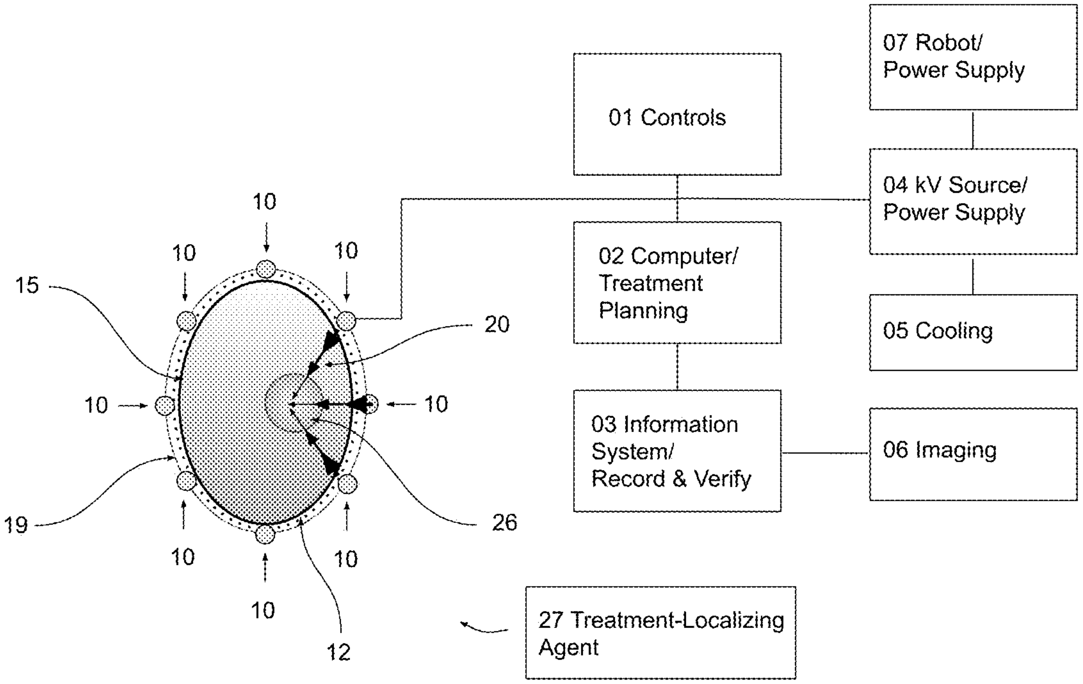
FIG. 5 (Short SSD - Lateralized)

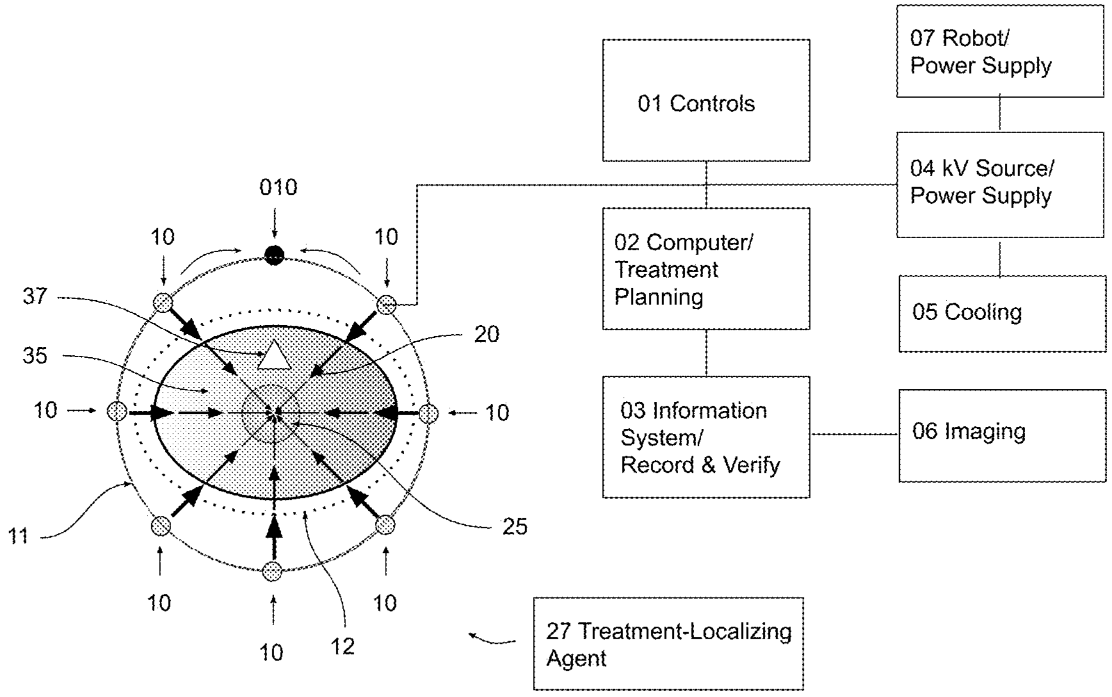
FIG. 6 (Critical Structure)

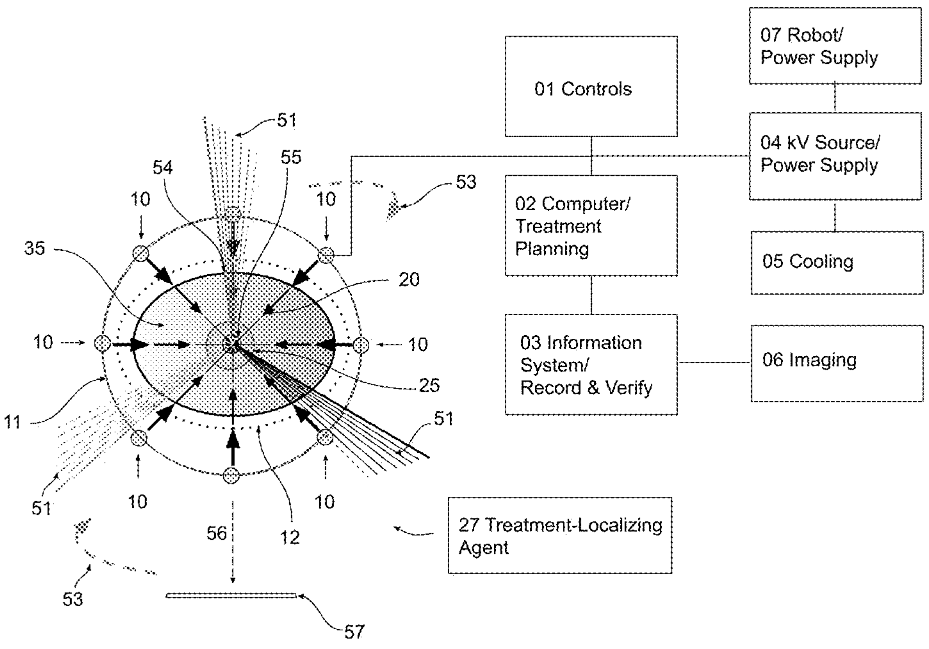
FIG. 7 (Long SSD - Out of Plane)

GRADIENT OPTIMIZED RADIAL TREATMENT (GORT)

RELATED U.S. APPLICATION DATA

This application claims priority of provisional application 63/303,222 with a filing date of Jan. 26, 2022.

REFERENCES CITED

U.S. Patent Documents

U.S. Pat. No. 7,481,758 January 2009 Weil and Morris
U.S. Pat. No. 11,099,140 August 2021 Goldberg et al.

Other Publications

Bazalova-Carter, et al., “Feasibility of external beam radiation therapy to deep-seated targets with kilovoltage x-rays,” Med Phys 44:597, 2017, AIP.

FIELD OF THE INVENTION

The claimed invention relates generally to medical therapy and imaging of lesions that are detrimental to a body and improving distributions of externally applied kilovoltage (kV) energy according to optimized gradients of radial-dose vectors. Situation-specific delivery parameters are optimized, then programmed to be implemented and precisely localized via mechanical automation. The system requires treatment with a kV source, which may also image via an opposing variable detector, to transfer and localize energy within a body. A circumscribing robot may enhance therapeutic and safety mechanisms.

BACKGROUND OF THE INVENTION

Treatment Optimization, Instant Registration and Localization. In contrast to drugs, ionizing x-ray beams do not have a therapeutic window based primarily on systemic dosage in a body. Rather their efficacy and toxicity are critically dependent on the relative and graded localization, in space and time, of the radiated energy that is deposited in given volumes of pathologic and normal tissue. Therefore, controlled and precise, externally initiated energy delivery, which is confined to be within the boundaries of a typical internal, moving lesion, is critical to maximize tumor or pathologic cell killing, and minimize healthy cell damage. Moreover, as opposed to pharmaceutical compounds, ionizing x-ray beams are capable of both imaging and treatment. However, taking advantage of multiple applications in a limited range of the x-ray spectrum is challenging. Usually deep-seated targets are not well visualized by conventional high energy (megavoltage, MV) treatment beams, nor treatable with conventional low energy (kilovoltage, kV) beams. Furthermore, therapeutic localization is complicated by uncertainty as normal and abnormal internal anatomy shift as much as 5 cm due to respiration, heart beat, peristalsis and patient positioning variability: The standard-of-care approach to these problems is to forgo real time lesion registration and instead to radiate an extra margin around a lesion to cover any setup uncertainty. This routine significantly enlarges a volume of normal tissue exposed to high dose radiation by the additional radius cubed, e.g., (4/3) *pi*r^3. As a result, the risk of serious side effects from excessive normal tissue dosing is greatly increased. Instead, inherent safety and efficacy are better addressed by optimizing system characteristics, including treatment parameters as well as employing a treating x-ray source that ideally also simultaneously performs real-time imaging and precise tracking of a moving, deep-seated lesion. Image-guided radiotherapy (IGRT) techniques such as cone beam CT, Retrieved from the Internet <URL: https://pubmed.ncbi.nlm.nih.gov/2128137/>, on-board imaging (OBI), Retrieved from the Internet <URL: https://pubmed.ncbi.nlm.nih.gov/12128137/>, stereoscopic imaging of fiducials, MV tomography and MR-linacs can image the anatomy and maintain registration. Retrieved from the Internet <URL: https://pubmed.ncbi.nlm.nih.gov/29116054/> Unfortunately, these methods do not provide instantaneous visualization, registration and synchronized tracking with a standalone treating x-ray source.

In order to facilitate an effective therapeutic kV x-ray source, a novel approach is recited herein. It is based on optimization of the dose gradients obtained with radial kV beams, which are concentrated in a lesion, and implementation with robotic tomography. The solution in the present invention unexpectedly enables ionizing kV teletherapy of deep-seated lesions with power management and cooling advantages over marketed x-ray technology: The beams' variables and parameters, which are optimized for a three-dimensional gradient field, include but are not limited to, energy, spectrum, filtration, field size, location and orientation in stereotactic space or volume, source-to-skin distance (SSD), generating amperage (mA) and time of delivery, beam shape and collimation, and number and location of beam overlaps, consideration of attenuation for a given beam energy and effects of the inverse square law (1/r^2) and inverse cube law (1/r^3). The variables and parameters of the focused, enhanced and localized ionizing dose or other energy deposition are optimized as gradient vectors or gradient vector fields. The present invention focuses multiple beams, considered as radial vectors or steradian-associated vectors herein, towards a location targeted in space and time, to deliver effective low-energy ionizing teletherapy. Wherein the radiated energy comprises a combination of ionizing output or beams selected from the group consisting of a range of dose gradients used for optimization to maximize function and efficacy. Delivery of the energy is done non-invasively without employing a device or mechanism to cut, puncture or traumatically penetrate skin or other surface, and without an open surgical procedure. As a result, the system can be surprisingly designed with a lightweight, air-, or water-, or oil-cooled kV x-ray source in a configuration capable of providing the aforementioned significant advances in function. The needed low-latency imaging and tracking is also possible. The system employs real-time lesion, or superficial, registration using visible surface imaging as well as portions of ionizing rays captured and reconstructed with tomosynthesis' for IGRT. Clinical and commercial applications of the technology in the medical realm for imaging, diagnosis and therapy include oncology. The optimized delivery of kV radiation induces a salutary effect in a diseased tissue comprising a combination of enhancing degradation, elimination, enhancing immune processing and antigen presentation of peptide elements. The induced effects of focused, enhanced and localized ionizing energy deposition further comprise a combination of enhancing tissue repair and removing tumors internally, each treating a diseased tissue selected from the group consisting of the head, body and other anatomy. The imaging and diagnostic capabilities may be used to initiate or enhance immunotherapy for oncologic or non-oncologic applications as well.

Radiation-based immunotherapy with systemic antitumor immunity may be initiated in one application of the present invention.

The effectiveness of radiotherapy depends on concentrating lethal radiation dose levels in a lesion without overdosing the intervening normal tissue, i.e., the dosimetry must conform to accepted clinical experience and expected outcomes. It is projected that x-ray treatments delivered by the present system will amply result in dosimetric conformity consistent with less side effects and better tumor control. In particular, by visualizing or registering the target lesion with the treatment beam and adapting to the lesion's movement coincident with therapy, the innovative system will allow higher standards of definitive and adjuvant therapy. Therefore, the combined functionality of imaging, tracking and treatment enabled with a single, lightweight, e.g., <60 kg, kV x-ray source, will yield more exact treatment, at higher effective doses yet with lower side effects and lower failure rates. The delivery of this unique performance with a single therapeutic modality and a single device is only available with the present technology or system. Furthermore, its utilization in vivo can be validated by Monte Carlo dosimetry simulations, which is not presently achievable with pharmaceutical agents.

Dosimetry with Monte Carlo (MC) simulations has validated the present invention's potential advantages compared to plans with 6 MV treatments using 3D-conformal radiotherapy (3D-CRT) and volumetric modulated arc therapy (VMAT). Models employed comparative treatments for lesions in the breast and lung. The simulated therapeutic regimens were based on standard protocols with a benchmark prescription dose to the planning treatment volume (PTV) and accepted limiting doses to normal surrounding tissue. These models demonstrated the overarching aim of the present invention to operate akin to MV sources could be met by optimizing energy; configuration, dose distribution and rate as taught herein.

In describing and implementing a new device, lung cancer, the leading cause of cancer mortality, can serve as a useful model system. There is very good imaging contrast between the normal lung parenchyma and most pathologic lesions, which is of importance for planning, treatment localization and follow-up evaluation. The lung also allows better depth-dose penetration of lower energy ionizing kV rays due to its lower density and corresponding lower attenuation. In addition, normal respiration results in sufficient excursion of normal tissue and tumors to require tracking capabilities during treatment. Thus, clinically useful implementation of a directed beam is enhanced by real-time evaluation of its therapeutic parameters. Since the normal lung is very sensitive to radiation and damage is readily documented with simple radiography, rigorous evidence and quantification of toxicity in 3D space is straightforward. Moreover, pulmonary lesions develop in a variety of sizes and shapes, which permit analysis of a range of dose-volume response criteria and outcomes. The application may employ advanced autosegmentation and volume rendering algorithms of x-ray images, which have been developed for use in other fields. This methodology forms a basis for lesion isolation and radiation dose targeting regardless of the background of normal structures. In addition to employing more generalizable and refined segmentation protocols for cancer in vivo, these solutions can be used to deliver deep kV teletherapy via appropriate distribution of kV photon flux. It thereby optimizes local therapy with better potential for regional and systemic cures.

Thus simulations were used to elaborate the physics supporting practical implementation of the invention herein, and enable a design of a clinical prototype. The required energy and shielding were relatively modest, along with the need for continuous power and dissipation of the associated heat load from a relatively compact device were also readily tenable. As a result, implementation does not require developing a new power supply, x-ray emitter, tungsten targets, robot or cooling system, but rather uses simple customized treatment collimation. The system design is workable and performs comparably to MV therapy at selected anatomic sites, e.g., bone, lung and breast, as measured by integral dose, sparing of vital organs, and delivering sufficient dose coverage of a lesion. The planning employs many radially distributed beams, which consistently yield clinically acceptable integral dosing similar to MV plans. This results from a balance between higher attenuation before a lesion but faster fall-off beyond the lesion at low versus high energy. The system as described herein treats a tumor plus margin with adequate dose distribution and dose rate. More specifically, it does not generate wide conventional radiotherapy portals covering regional lymph nodes. In addition, the present invention intentionally plans for significantly more heterogeneity of intratumoral dosing. i.e., more peaked, than the plateaued, compared to the uniform tumor dose used with volumetric modulated arc therapy (VMAT). The former method derives from the clinical evidence that there is likely to be improved tumor control using the more peaked Gamma-Knife or linac-based dose distributions employed for radiosurgery. Retrieved from the Internet <URL: https://pubmed.ncbi.nlm.nih.gov/16209896/>, <https://pubmed.ncbi.nlm.nih.gov/19414667/> For example, a prescription for VMAT with D95=38.5 Gy can be very uniform in the lesion, e.g., D50 is close to 40 Gy, while a prescription for kV arc therapy (KVAT) with D95=38.5 Gy can rise sharply in the tumor, e.g., D50 is close to 50 Gy. The dose-volume histograms (DVHs) of the surrounding normal tissue are expected to be similar, and clinically acceptable with both techniques, however, intralesional dose is substantially greater with KVAT. The present invention takes advantage of this intuition for potential application in increasingly employed regimens, such as, lung cancer radiosurgery and accelerated partial breast radiotherapy. It follows then that both the dosimetric distribution and dose rate via computational optimization strategies recited in the present invention, as well as the associated hardware improvements, are unexpected and distinct from prior art.

The present invention employs hardware and software for instantaneous tumor tracking via real-time, beams-eye view capabilities. This functionality can readily be demonstrated on dynamic chest phantoms to validate the clinical performance of the system for treating human or spontaneous veterinary tumors. Investigational x-ray labs routinely employ static and dynamic radiometric phantoms, including dynamic anthropomorphic chest phantoms (e.g., N1. "Lungman." Kyoto Kagaku-America, Torrance, CA). These devices are used with flat panel detectors and radiochromic film dosimetry (GafChromic™), Ashland Advanced Materials, Bridgewater, NJ) for experimental validation of the an x-ray system's imaging, e.g., cone beam and tomofluoroscopy; and its therapeutic dose rate and dosimetric distribution. In addition, internal telemetric evaluation of a beam's quality; output, anode cooling and radiation leakage are possible during routine employment. An iterative process thus improves evaluation of the performance envelope of a system and measures its dosimetry in phantoms. Such complementary MC and analytic studies for characterization of the x-ray emissions can be utilized in prototype engineering design and field testing. Thus, it is relatively straightforward to assess the practicality of important metrics such as dose rate and distribution for treating clinical lesions.

Computational models derived from prototype hardware and software also make it possible to validate the image reconstruction and treatment simulation algorithms in less controlled settings. It can confirm that the apparatus functions meet clinical standards. For example, chest phantoms allow analysis of focused lung tumor treatment and are useful in preparatory design of complementary solutions. However, the endpoint of such analysis as taught herein is to demonstrate quantitative support for integrating multiple functionality into a single treating system. Thereby, it can support that presumptions and engineering are sound. Specifically; documentation includes but is not limited to the following: i) the image quality for cone beam and tomofluoroscopy, e.g. Noise Power Spectrum (NPS) and Modulation Transfer Function (MTF), ii) the duty cycle for the source, especially as pertains to heating, and iii) the therapeutic dose rate and distribution to normal tissue and tumors. Film dosimetry can confirm both geometric and quantitative contributions of the multiple optimized gradients of radial beamlets. The accuracy of the computational studies compared to the actual source output is thus verified and validated as per past studies.

The present recitation of treating deep sites non-invasively requires optimization and integration of parameters, controls and networks. It is possible that subsystem components from different manufacturers will operate together with unforeseen variations. Advanced controls and networking as described herein to assure proper function of each subsystem by itself, and in combination with other parts, is therefore necessary. In early development, e.g., one-off prototypes, there may be pitfalls and alternatives, including long lead times for replacement parts, which could impede integration of subsystems as well. In that case, alternative materials and parts might be repurposed in a modular fashion from pieces of existing, similar systems.

Optimization of a collimator in the present invention is determined by well-understood computational dosimetry. Collimator design is based on efficiency and manufacturability and is performed with both MC and analytic methods. The extension of such studies provides insights into the trade-offs of beam characteristics, including but not limited to output and lateral beam falloff. Collimators can be manufactured by different methods, e.g., casting, 3D printing. Materials and methods are assessed for strength, case of handling and cost. The designs may vary based on entrance and exit aperture size, multileaf collimator (MLC) vane dimensions, septal wall (if any) thickness and material composition. To validate the design output, dose distributions and falloff, radiochromic film dosimetry can be measured as well. Computational optimization of such variables, as flux throughput efficiency and penumbra, can also be accounted for when determining a collimator's dimensions. Thus, it is possible to assess many different potential parameters for given clinical scenarios, e.g., tumor size and depth, optimal dose rate and beam spread, using algorithms that minimize loss or cost function. On the other hand, handling certain materials and the machining techniques can present uncertainty; which is most often addressed by employing acceptable replacements.

SUMMARY OF THE INVENTION

It is well known that due to their high skin dose and fast absorption in tissue, medical use of kilovoltage (kV) beams is limited to imaging and radiation treatments of superficial lesions. In view of that, kV x-ray beams heretofore have been unworkable for treating deep lesions in a body. It is general knowledge that megavoltage (MV) systems deliver excellent dose distribution in patients and are the gold standard for external beam radiotherapy. At present, MV linear accelerators are used to treat most cancers, though kV x-ray devices are much less complex and costly. These positive attributes prompted a re-evaluation via simulations of this extensively used kV technology. The present invention derives from validated computer simulations, and can be demonstrated to be comparable to conventional systems in potential safety and efficacy. Available medical physics can be applied to proof-of-concept computer models, dosimetry and image-guidance solutions.

Different techniques and geometries for kV sources can be studied with computer models. Evaluations are readily made to optimize depth-dose delivery and absorbed dose at the skin and reveal the potential to treat deep lesions. Unexpectedly the present invention enables application of kV x-ray technology to both image and treat cancer well below the skin with a single source. The x-ray system recited herein addresses kV shortcomings by rapidly optimizing energy employed, and other parameters, to properly distribute multiple kV beams via mechanical robotic manipulation. Thus, a single kV system as shown by Monte Carlo modeling would surprisingly be found to be practical to both image and treat any target in the body using accepted dosing algorithms. The source can create CT scans for planning and image in real-time during therapy with or without a separate CT unit. Clinical tests and simulations suggest the design can plan and complete effective therapy within 1 hour. A separate CT unit is not required as the cone-beam CT (CBCT) imaging for the present invention can be used surprisingly for treatment planning. These projections yield equivalent performance to a $6M CyberKnife® at 3% of the cost per system, and cost per patient of $100 or perhaps less. Development of such a validated, robotic system will provide ready access to a well-established treatment for patient populations in need. Given the contrary conventional teachings about the safety and efficacy of therapeutic kV x-rays, the present approach is a radical departure from accepted strategies, and as such is unexpected and highly innovative.

Therapeutic x-rays work by delivering a known quantity of energy to a given mass of tissue. This is measured in joules per kilogram, which is defined in gray (1 Gy=1 joule/kg). The energy of a beam determines its interactions with matter and range from the photoelectric effect to Compton scattering in the spectrum used for medical applications. Megavoltage (MV) x-rays are characterized by a "build-up effect," where initial penetration through the skin deposits less dose than the concentration of extra dose a centimeter below the skin surface. Therefore, MV x-rays can be used to treat deeper lesions relatively safely since the skin does not become burned and they are more penetrating than kV. On the other hand, kV x-rays have a significantly higher probability of interaction with matter, i.e., a higher cross-section. They are thus more composition sensitive than MV beams, and tend to maximally deposit their dose upon entering the skin. Furthermore, as they penetrate the body; they undergo significant attenuation of the x-ray flux and dose at depth. The present invention overcomes the detriments of kV beams at depth while delivering safe and effective distributions of x-ray dose absorption.

In addition to x-ray beams experiencing attenuation through interactions with matter, the intensity of the beams are affected by the distance from the source by the inverse square law; (1/r)ˆ2. A source emitting x-rays at a range of distances, e.g., 0.4-1.0 m, will maintain its spectrum but deliver fewer photons upon reaching the skin, i.e., lower dose and dose rate. Once they hit the skin, the x-rays will affect tissue differently depending on the overall length of travel relative to a range of depths for lesions in a body; e.g., 5-15 cm deep. For a given depth below the skin, greater source-to-skin distance (SSD) yields better dose deposition relative to the surface, but a lower dose rate. And, for a given depth below the skin, lower source-to-skin distance (SSD) yields poorer dose deposition relative to the surface, but a higher dose rate. Thus, the probability of interaction with matter is dependent on energy, and the inverse square law is dependent on distance. They both are accounted for in clinical MV radiotherapy. But, these parameter trade-offs are critically important for enabling clinical kV radiotherapy, influencing its distribution of dose and the rate of delivery of dose. The present invention is unexpected because prior to it, safe and effective kV radiotherapy employing a distant or non-invasive source, teletherapy, was not deliverable to deep-lesions.

In clinical ionizing radiotherapy, treatment can be delivered over short distances via interstitial or intracavitary routes. Such procedures are frequently invasive and use radioactive materials or miniaturized electronic x-ray tubes. These short-range techniques are classified as brachytherapy and deliver significantly tighter radiation dose distribution than is possible with non-invasive beam-generating sources such as linear accelerators. The latter technique of external ionizing beam delivery over distances on the scale of 0.2-1.0 m (from source to skin or tumor) is classified as teletherapy. The numerical distance of far-versus near-radiotherapy is not well classified.

For a kV x-ray source to be useful for the treatment of deep-seated lesions it must compensate for the rapid falloff of a beam's flux due to greater attenuation while not exceeding the threshold of significant skin damage. This is most readily achieved by distributing multiple beams, which are non-overlapping at the surface, and converging on a lesion deep in the body. For example, a single beam with a dose at depth that is 20% of its surface dose can be distributed into 10 beams (without overlapping upon entry) that all converge on a lesion at depth. In this instance, a tumor accumulates twice the dose of each entry point, which could enable safe and effective therapy. By using 30 distributed beams in this case, the lesion-to-skin ratio would increase to 6:1, which would be well tolerated in almost all cases. Thus, wide distribution of rays with a point, region or volume of concentrated, or focused, intersection supersedes losses due to attenuation. The delivered radiation may be individual or arcing beamlets in the same plane or in different planes, e.g., non-coplanar, to achieve a satisfactory spread of the entry dose and useful lesion-to-skin enhancement. A kV x-ray source delivering teletherapy in the body in this may be mounted on a rotating gantry, or preferentially a robotic arm, to achieve mechanical distribution. In another embodiment, multiple kV sources could be moved or rotated around a focal point within a lesion. The entry point of the kV x-rays might also be manipulated by charged particle optics, prior to x-ray generation, spreading out the origins of photon release along with significant collimation to narrow the distribution of photons.

As noted, at greater SSD, the lesion-to-skin dose ratio as derived from the percent depth dose (PPD) is optimal, but flux or dose rate is decreased. The lower dose rate is impractical for clinical applications if too low and results in lengthy treatment times. Decreasing the SSD rapidly increases dose rate by rˆ2, but, too short an SSD will decrease the lesion-to-skin dose ratio to unsatisfactory levels. To achieve satisfactory kV treatment plans, it is necessary to optimize these multiple parameters simultaneously as recited in the present invention. Significantly, the SSD must be shortened and many planes of treatment must be employed compared to conventional treatment with MV beams. Thus, the distance of the treating source from the lesion as recited in the present invention is equal to, or between the distance employed for conventional teletherapy and that employed for conventional brachytherapy. However, the kV system retains non-invasive, non-radioactive functionality.

This invention entails optimized therapeutic kV x-ray beams for the body or head that can locally deposit different energy doses and gradients. This may include, but is not limited to, targeted delivery of ionizing energy within a body that can be used to definitively treat, or deploy and enhance other treatments, such as molecular compounds, nanoparticles, antibodies, biologic agents, immunologic modifiers and small proteins. One aim is to assist oncologists, employing either pharmaceuticals or therapeutic devices, who require improved and more reliable modalities to verifiably localize and decisively treat cancerous masses across the gamut of presentations of the disease and treatment factors, i.e., anatomical, pathological, normal tissue sensitivity and clinical scenarios. Neither isolated imaging nor isolated therapeutic techniques alone achieve this benchmark. Retrieved from the Internet <URL: https://www.ncbi.nlm-.nih.gov/pmc/articles/PMC3397279/> However the novel integrated system taught herein, by combining the enhancing performance of the different methods, unexpectedly allows effective clinical applications of kV x-rays. Combined imaging and therapy by a single non-invasive, low-power x-ray source improves the therapeutic window by explicitly conforming to tissue borders and tolerances of absorbed energy. As a result, there is a significant potential benefit of real time feedback from cancer treatment as it is underway. Thus, safety and efficacy are enhanced and the system works more reliably in primary and adjuvant therapeutic settings.

The invention uses lightweight, low energy sources under the control of a robotic arm to expand the range and orientation of the kV source's discharge from a 5-mm-spot tungsten anode. U.S. Pat. No. 11,099,140 teaches an imaging-only system for computed tomography with a robotic arm that moves an X-ray emitter around a subject and an detector that captures 2-dimensional views. A processor uses computed tomography to reconstruct an image from the 2-dimensional views. The robotic arm varies the pitch of the emitter to improve the spatial resolution. However, in the present invention, it is notable and not obvious that the resulting large non-coplanar or 3D radial distribution of the beams' origins, combined with their ultimate focus in a deep-seated lesion, provides a unique geometry of kV photon beamlets. Delivery can be adjusted by intensity modulation, e.g., the x-ray source emission time, distance, current and collimation, at any point in the mechanical sweep around the lesion, which is precisely controlled by the robotic system. This enhanced control, along with low energy; significantly simplifies the demands on collimator performance and allows for simpler collimator designs. For therapy; x-rays are collimated per source orientation relative to a tumor while beamlets are made to continually converge to a focus in a lesion deep in a patient's body. The process entails mechanically manipulating multiple converging beams, precisely and swiftly; around a patient's body or head. There is no overlap of beams at the surface entry and beamlets are accurately maintained focused at a lesion. In this way, it is possible to satisfactorily deliver kV dose to deep-seated, moving lesions with substantially reduced skin dose. Retrieved from the Internet <URL: https://pubmed.ncbi.nlm.nih.gov/28133751/>

Computational manipulation and optimization of kV x-ray beams' spatial distributions, weighting and associated dosimetry can demonstrate the feasibility of non-coplanar techniques in various clinical scenarios. Though they have not yet been developed for radial gradients, significant improvement in lesion dosing with reduced dose to critical structures has been projected via inverse optimization, using machine-learning treatment planning algorithms. Such optimization programs can sort out the ideal weighting for each beamlet position and flux based on dose constraints derived from conventional treatments. In addition to MC models, inverse plans are routinely evaluated with radiochromic film in radiometric phantoms to validate both dose rate and dose distribution as noted above. Meeting or surpassing advantageous dosing characteristics with inverse planning, and quantitative demonstration of functionality with film, thus can validate MC modeling of the x-ray source in the present system. Its effectiveness at different anatomical sites can be derived from treatment planning that meets standard-of-care dosimetry regimens i.e., cooperative group breast or lung cancer protocols.

Moreover, to optimally integrate the system's software and hardware, complementary analysis of subsystems may be employed. For example, the low-energy; low-amperage, near-field x-ray beam source is capable of both therapy and advanced tomographic imaging, which enables visualization of dosing regimens. The imaging functions include cone beam CT for registration, diagnosis and planning, tomosynthesis for real-time beams-eye viewing, along with real-time lesion tracking, and simultaneous therapy. At present, no other system has all these capabilities, or enables the complete radiosurgical workflow in one device. A flat panel detector array opposite the source can be positioned to capture registration data and data for image reconstruction (including 3D volume rendering) or intrafraction monitoring during treatment delivery. For the latter technique, the present system can employ tomofluoroscopy; a novel imaging technology when used with radiotherapeutic delivery.

Treatment Uncertainty. It is an object of this invention to provide a method to better manipulate kV x-ray beams as well as reduce treatment uncertainty. The importance of optimizing radiation dosimetry is central to radiotherapy planning and delivery. The complexity and cost of standard systems, using a variety of derivative imaging methods, Retrieved from the Internet <URL: https://pubmed.ncbi.nlm.nih.gov/29237965/> falls short of providing both the visualization and targeting capabilities of the technology recited herein. For example, on-board, cone beam imaging, e.g., Varian's On-Board Imager® (OBI), does not yield adequate resolution of lesions, while MR imaging cannot be performed for a beam's eye view (BEV) from the treatment source and only provides 2D information with a significant latency. In addition, stereotactic radiography aligns primarily on external fiducial markers, and MV tomography has less certainty in tumor tracking than available low-energy imaging systems. Retrieved from the Internet <URL:https://pubmed.ncbi.nlm.nih.gov/25979029> In practice, these systems guide corrections of patient registration or alignment errors, but they are not instantaneous and cannot adapt quickly enough to cover movement due to physiologic processes, which may occur when a treating beam is on. These limitations of standard radiotherapy systems to identify and follow a lesion in a clinical setting can significantly impair the required targeting of a treatment volume and jeopardize the reliability of a prescribed radiotherapy regimen. Since most radiation treatments deplete normal tissue tolerance locally; the one-time-opportunity to cure a cancerous mass is put at unnecessary risk. On the other hand, the system presently taught utilizes near-field kV teletherapy with incumbent tomography. The hardware is an order of magnitude less heavy than top-of-the-line linear accelerators or modern CT scanners. There has been steady improvement in related imaging.

Distributed Low Power, Maintenance of Focus. The present recitation overcomes limitations of composition-sensitive kV ionizing radiation by remotely and robotically introducing mechanical movement of the source in unexpected, extended non-coplanar volumes per optimization of radial x-ray beam vectors. In addition, the x-ray source recited operates relatively efficiently and therefore is more readily cooled than conventional designs because its low power, low energy and low amperage, only require modest air, water or oil heat dissipation. The present invention advantageously employs continuous modest power with more optimal energies over prolonged periods for both imaging and therapy. As a result of optimized radial beam gradients, the present system is able to expand on proven technological experience and robotics. By applying an enhanced solution of beam paths and parameters as a clinical platform, the present invention overcomes significant shortcomings in delivering precise, safe, and controlled radiotherapy.

Safe and effective delivery of ionizing kV teletherapy with 100-350 kV to lesions located more than 1 cm beneath the skin surface, i.e., deep-seated, has been considered infeasible. This is due to the x-ray spectrum's composition sensitivity with high cross-section and greater probability of interaction, which results in rapid fall-off of flux beneath the skin. In past practice, non-invasively achieving adequate dose to a deep-seated lesion, >1 cm below the skin, has resulted in overdosing the more superficial tissue, which is irradiated en route by a therapeutic beam and burns the skin. Distributing the incident beams over a greater surface area while maintaining localization and concentration in a lesion can reduce the surface dose. However, that approach results in a high integral (normal body+lesion) dose, long delivery time and requires very high power. Widely distributed, high power, high flux beams have thus far only been simulated. Simulation of the methodology has shown clinically adequate dosimetric distributions. Retrieved from the Internet <URL: <https://pubmed.ncbi.nlm.nih.gov/23093305/>, <https://pubmed.ncbi.nlm.nih.gov/28133751/>, <https://pubmed.ncbi.nlm.nih.gov/28986987/> Presently, successful construction of such a design with clinically useful performance parameters has not been achieved. The geometry of an inverted pyramid, with the apex in a lesion and the base covering the skin entry sites, was evaluated as a beam distribution zone. Though the geometric disbursal improved the lesion-to-skin kV-dose ratio in models, it entails radiating an excessive volume of healthy tissue with very high flux, e.g., mAs. In one simulated example, 200 kV at 200 mA over 30 minutes was used to treat at 5-cm depth. The present invention is unexpected since it optimizes a much lower flux, mAs and power to achieve a clinically useful treatment plan for deep-seated lesions, e.g., >1 cm below the skin. The system conflates a therapeutic maximum and a toxicity minimum by employing optimized dose gradients and validated paths, parameters, energy, beam direction, mechanical control and skin-to-surface distance (SSD), for clinically advantageous dosimetry and dose rate in deep-seated lesions.

The Gradient Optimized Radial Treatment (GORT) system contains six major components:

i) X-ray source and power supply optimized for delivery of useful kV energies for imaging and treatment, wherein flux gradients are varied by manipulation of source parameters;
ii) Collimation and output ionization chamber simplified for better control of dose delivery deep in the body;
iii) Robotic control of source movement using simple existing automation and power supply;
iv) Cooling with low-power air, water or oil circulation;
v) Software and drivers for operating, image reconstruction, planning optimization, dosimetry and beam delivery. Integrated subsystems for practical implementation; and
vi) Detectors to create a CT image and perform real-time imaging during therapy.

Benchmark innovations of the present system include, but are not limited to, computational algorithms to optimize dose gradients by adjusting system controls and parameters in case-specific treatment protocols. In contrast to image-guided MV radiotherapy, the approach herein conforms to ideal treatment protocols by using independent units (stand-alone technology) to build a more complex structure and functionality. Thus the present invention enables delivery of more advantageous kV dosimetry derived from vector optimized treatment configurations, which include beam path as well as source orientation and distance.

The kV system is capable of imaging, tracking and treating operations with a single x-ray source. CT or MR cannot use the treating beam to image structures of interest. Moreover, internal or external fiducial markers can sometimes be used to track moving lesions. On the other hand, a combination of the radial vector or steradian-associated vectors using gradient optimization, taught herein in one system, complements x-ray functionality and permits therapeutic and diagnostic kV x-ray use in a clinical setting. The system can perform real-time cone-beam CT and tomofluoroscopic imaging. Localization of the treatment focus is obtained by analyzing the variance between pre-treatment planning images in comparison to beams-eye images during treatment. The system optimizes which variables and treatment characteristics are key to minimizing loss function.

The system herein combines mechanical movement with robotic control to spread out kV surface dose while maintaining focus on a deep-seated lesion. It quickly generates widely distributed converging beams from multiple angles along with restricted movement of the source across a prescribed, limited range to optimize dosimetry and safety. The devices herein use relatively low power and thus require only modest cooling of the x-ray source. This allows lengthy intervals of continual beam-on time for accurate dose localization during treatment. In addition, the system delineates lesions by autosegmentation and computes optimal beam delivery based on accurate registration, collimation and tracking. Moreover, the system performs verification and validation of the planning derived from real-time image data.

The present invention works by aligning the energy-emitting source with a target lesion using a robot in a localized, or circumferential, or ring or spherical distribution around a patient, or in a surface conforming route as a customizable arrangement. It can operate employing an array of the ionizing energy source positions, electronically or computer controlled, to shift and contour their output in different directions by automating and moving the sources, for discrete and localized delivery of energy dose to a given depth or lateral position in the body with a narrow or focused distribution. The system makes possible contouring energy output or beams to concentric, converging electromagnetic energy beams and depositing energy dose in a localized volume of interest to treat pathologic tissue. It comprises controlling the sources electro-mechanically or with computers and drivers, and operating with a connected power supply and cooling. As a result, it takes advantage of depositing energy dose locally by shifting and contouring energy output, or beams, for treatment comprising a combination of pathologic lesions, each having a detrimental impact selected from the group consisting of cancer, cancerous and benign tumors and mass effects.

The GORT system focuses the output of an array of x-ray source positions on a diseased volume of anatomy to ablating levels in a range of 18 Gy or greater in single fractions, at 24-hour intervals for example. The positions are distributed along the radials for different spherical volumes emanating from a center in a targeted lesion encased in normal anatomy. The anatomy comprises a combination of sites selected from the group consisting of head, body or extremities. Targeting a lesion within a body is done by employing volumetrically discrete energy dose deposition around the lesion to beneficially damage pathology. The conforming volume of prescribed x-ray dose is discrete, encompassing and customized to a detrimental phase or lesion within the body, thereby enhancing restoration to healthy states by controlling parameters to a normal physiologic range and thereby enabling a healthy transition state. A resulting adjustable radiation field size can cover an internal treatment volume having diameters ranging from millimeters to a plurality of centimeters.

The system further comprises arraying x-ray source positions around a pathologic site to focus and enhance kV range energy within an optimized portion of steradians of dose distribution. The optimized steradians of dose distribution are centered in a sphere of possible source positions with a surface area equal to the radius squared. In other words, the system uniquely treats with beams along the radii of optimized radiation dose gradients, which diverge from a common center located in a targeted lesion. In this application as well, the beams' variables and parameters, which are optimized for a three-dimensional gradient field, include but are not limited to, energy; spectrum, filtration, field size, location and orientation in stereotactic space or volume, source-to-skin distance (SSD), generating amperage (mA) and time of delivery; beam shape and collimation, and number and location of beam overlaps, consideration of attenuation for a given beam energy and effects of the inverse square law (1/r^2) and inverse cube law (1/r^3). The kV therapy is delivered by implementing the variables and parameters with automated mechanisms such as robots.

BRIEF DESCRIPTION OF THE FIGURES

The construction and usage of embodiments will become readily apparent from consideration of the following specification as illustrated in the accompanying drawings, in which like reference numerals designate like parts, and wherein:

FIG. 1 is a diagram illustrating a system according to some embodiments, which shows a long SSD to improve dosimetry to the head:

FIG. 2 is a simplified perspective view of arrayed source positions and delivery components according to some embodiments, which shows a long SSD to improve dosimetry to the body:

FIG. 3 is a diagram illustrating elements of arrayed source positions according to some embodiments, which shows a shortened SSD to improve dose rate to the head:

FIG. 4 illustrates elements of arrayed source positions according to some embodiments, which shows a shortened SSD to improve dose rate to the body:

FIG. 5 illustrates elements of arrayed source positions, which shows a shortened SSD and curtailed beamlet numbers to treat the head and CNS with an energy dose localized to a lateral position in a focused distribution:

FIG. 6 illustrates elements arrayed source positions, which shows a long SSD to improve dosimetry to the body, wherein the pattern of source output is effectively directed towards a desired location and energy traveling towards critical structures are quenched: and FIG. 7 is a simplified perspective view of arrayed source positions in and out of plane as well as delivery components according to some embodiments, which shows a long SSD to improve dosimetry to the body.

DETAILED DESCRIPTION OF THE INVENTION

The construction and usage of embodiments will become readily apparent from consideration of the following specification as illustrated in the accompanying drawings, in which like reference numerals designate like parts, and wherein:

Local and Regional Radial Dose Gradient Deposition. In the case of malignant disease or other pathologies of the CNS, there are several therapeutic, ameliorating approaches that can be employed around the head 15 as shown in FIG. 1, or body 35 as shown in FIG. 2 with vectors of ionizing energy 20 of electromagnetic waves in the 100-350 kV x-ray range. In the figures, the magnitude of the dose intensity gradients as they vary enroute as well as their direction are represented by the thickness, length and orientation of the arrows, which denote vectors of ionizing energy beams 20. They thus can be altered by factors described herein that affect the dosimetry and dose rate of kv x-ray beams. Conventional radiotherapy gantries restrict beam paths and distances mostly to fixed planes around an isocenter and at fixed source-to-axial distance (SAD). Therefore, modification of these factors relative to the spherical radials originating from a focal point in a targeted tumor is unrealized. In the present invention, non-invasive, i.e., delivered without employing a device or mechanism to cut, puncture or traumatically penetrate the skin, and without an open surgical procedure, external kV energy 20 can be delivered to a pathological region or lesion 25 of the body 35 as shown in FIG. 2, including the head 15 and CNS as shown in FIG. 1, by the spectra and modalities including, but not limited to, the above mentioned electromagnetic waves and oscillations. With these methods the mechanisms of treating disease can entail, but are not limited to, causing necrosis, induction of apoptosis, induction of heat-shock proteins, decreased blood flow, increased permeability of the blood-brain barrier (BBB) to permit entry of beneficial effectors, initiating immune responses (stimulating or suppressing), and causing euphemistic electromagnetic or chemical interactions. By way of the present invention, non-invasive, external kV energy sources 10 are aimed to a focus 55 and may employ adjustable or phased array of source positions to contour different locations, shapes, sizes, frequency and timing, and other treatment related parameters, of the energy output. The beam location and orientation may be set with automated mechanical movement of the sources to optimize the dose gradients of radial paths emanating from a focal point 55 within a lesion 25. The energy is thereby concentrated in a targeted volume, enhancing the delivered dose and made discrete, and thereby encompassing of a detrimental lesion 25. A treatment volume can be maintained or adjusted, spatially and temporally, to cover specific pathology; anatomic and functional structures, or regions of interest. The resulting adjustable radiation field size covers a localized, or regional, internal volume 25 having diameters ranging from millimeters to a plurality of centimeters. A distribution of external energy radiating source positions 10 may be in a localized, or circumferential distribution, or a ring 11 or non-coplanar spherical distribution around a patient's head 15, CNS or body 35. The patient's surface is not cooled with circulating air or water 12, nor coated with a conductive gel. The illuminated treatment volume 25 can be maintained or adjusted to cover specific pathology, anatomic structures, or regions of interest. The process and time of treatment delivery may be continual, or fractionated over hours, days or weeks via standard source positions 11. Given the variety of energy source 10 orientations and positions possible with the present invention, they might be selected based on the efficacy of maximizing their intensity. The energy sources 10 are connected to a power supply 04 with cooling 05 and utilize computerized controls 01. The power supply 04, can be connected to a microcontroller to provide a means of regulating the sources' intensity and timing. The treatment system includes a computer with treatment planning software (TPS) 02, which can upload images 06 for planning and guidance, and is connected to an information system with record and verify software 03. The TPS consists of a medium storing computer-executable process steps to reconstruct medical images and calculate therapeutic effects of the localized ionizing kV radiation of energy treatment, i.e., it has a kV dose "engine." In some configurations, the system includes a treatment table or chair, capable of movement in three dimensions, and source-exit monitoring to measure radiation output at the source window. In some embodiments, the system of the present invention comprises treatment of diseased tissue 25 with a ionizing-radiation, treatment-localizing agent 27, which becomes active in response to received ionizing-radiation energy 20. Such ionizing-radiation, treatment-localizing agents 27 include, but are not limited to, high-z radiographic contrast agents, and liposomes, which carry drugs, biologics, immune-modulating compounds, or contrast agents, and microbubbles.

It is an object of this invention to provide a method for depositing kV energy into a discrete, conforming volume encompassing and customized to a detrimental phase or lesion deep within a body, and thereby enhancing restoration of controlling parameters to a normal anatomic and physiologic range, thus enabling a healthy state. By example, a non-coplanar array of energy source positions at along SSD, are spread out around a head 15 as shown in FIG. 1, or body 35 in FIG. 2, or moved by a robot, or at a short SSD for the head 15 demonstrated in FIG. 3 or body 35 in FIG. 4. The kV source 10 is connected to a power supply. In some examples, the source positions 10 are in a non-coplanar array, wherein the source is moved around the lesion it stays focused on. To treat pathologic lesions, the ionizing kV source can be robotically controlled to shift and contour their output, e.g., beams 20 in this instance, in different directions. Thereby, x-ray dose is delivered discretely and localized to a given depth or lateral position in a body 35 or head 15, illustrated in FIG. 5, with a narrow or focused distribution. The optimized gradient underlying possible source locations 10 in this invention is distributed among a reachable spherical space 11 around the body or CNS. The pattern of the beams 20 is effectively focused towards specific or selected volume 26, and x-ray energy traveling towards undesired locations 37 as shown in FIG. 6, e.g., healthy tissue, are quenched. The overlap in a lesion of directed waves builds up energy deposition in the focus volume 25, which has been delineated beforehand by imaging 06 to receive an enhanced dose of the energy or radiation. The effective and deliberate targeting with ionizing energy to specific volumes of focus 25 or, locations 26 in FIG. 5, deep inside the body 35 or head 15 is measured and evaluated in real time with imaging, including kV tomofluoroscopy. The purpose of the focused and enhanced energy deposition 25 is to reset or disable, including but not limited to: cancers, pathologic physiology or structures, nerve pathways. In addition, the delivery of locally augmented energy can be used to enhance: immunity; the presence of chaperone molecules, e.g., heat shock proteins (HSPs, sHSPs), the delivery of energy-sensitive compounds or pharmaceuticals, carriers, and energy-sensitive vesicles, e.g., thermolabile liposomes or microbubbles.

The term gradient as used herein is an increase or decrease in the magnitude of a radiation dose (in Gy) from one point to another. It is furthermore the calculated or measured change in value along a graded difference on an axis originating at a focal point or common center 55 of a spherical radial distribution 51 as shown in FIG. 7. In the present invention the center 55 is set inside a tumor 25 and the radials 20 emanate outward through the body to potential source positions 10. Multiple beams 20 can be considered as radial vectors or steradian-associated vectors. The term steradian as used herein is a solid angle at the center 55 of a sphere subtended by the surface area of the radius squared.

Kilovoltage radiation is composition-sensitive and rapidly attenuates in the body with a maximal dose near the entry point 54. X-rays 56 passing through the body 35 can be collected by detectors 57 opposite the source 10 for image reconstruction. At clinically relevant depths of 5-10 cm, beam falloff can be as much as 90% of the surface intensity. These significant interactions are due to absorption via a body's mass-energy attenuation coefficients for a given energy spectrum, as well as the geometry of the beam flux flowing from the radiation source 10. In this case, higher energy, or more filtered, "harder" beams are more penetrating. The position and orientation of the x-ray source 10 can significantly be optimized to make kV treatment dosimetry unexpectedly safe and efficacious. These geometric considerations can also be employed to produce a clinically satisfactory kV treatment plan. For example, a lesion at 10-cm depth treated with a single kV beam might receive 10× less dose than the skin 54, i.e., its ratio of lesion-dose versus skin-dose would equal 0.10. A straightforward application of 10 focused beamlets, each of 1.0× dose and distributed with no overlap, in or out of plane 53, at the surface entry 54, would yield a lesion:skin dose ratio of 1.0 for each beamlet. Additionally, 100 such focused beamlets would yield a lesion:skin dose ratio of 10.0 for each beamlet. Thus, a significant problem can be solved by geometric distribution at the surface 54 with focus 55 at depth in a tumor 25. Geometric advantages can also be gained in accord with the inverse square law, which can affect both dosimetry and dose rate. This is demonstrated with manipulation of the SSD for a given tumor depth as shown in FIG. 3 and FIG. 4. In this example, a 5-cm deep tumor treated at an SSD of 45 cm will have a depth dose (relative to the surface) of (45/50)^2=0.81. In comparison, treatment at an SSD of 20 cm will have a depth dose of (20/25)^2=0.64. Therefore, greater distance from the source improves the dosimetry at depth and reduces relative falloff from the skin dose. Thus, for a given system parameter, e.g., SSD, relative falloff from the skin dose along any given radial 20 coming from the targeted tumor 25 can be optimized as radial vectors or steradian-associated vectors. In a similar way; amperage and SSD alterations might be used to tune the dose rate. Optimization along the gradient of the vectors for the system parameters and characteristics can significantly improve the dose distribution, rate of dose delivery, or other operational metrics as taught in the present invention.

The beams' variables and parameters, which are optimized for a three-dimensional gradient field, include but are not limited to, energy, spectrum, filtration, field size, location and orientation in stereotactic space or volume, source-to-skin distance (SSD), generating amperage (mA) and time of delivery; beam shape and collimation, and number and location of beam overlaps, consideration of attenuation for a given beam energy and effects of the inverse square law (1/r^2) and inverse cube law (1/r^3). The variables and parameters of the focused, enhanced and localized ionizing dose or other energy deposition are optimized as gradient vectors or gradient vector fields. Accordingly, the present invention focuses multiple beams, considered as radial vectors or steradian-associated vectors herein, towards a location targeted in space and time, to deliver effective low-energy ionizing teletherapy. Wherein the radiated energy comprises a combination of ionizing output or beams selected from the group consisting of a range of dose gradients used for optimization to maximize function and efficacy.

Gantry-mounted conventional MV therapy machines are unable to move in-and-out along the radial orientations without interrupting a procedure and setting up the patient in a revised position. On the other hand, the system and methods taught herein can optimally adjust in real time along any of the radial gradients 20 of the stereotactic space around a targeted lesion in a patient. This is most readily achieved by integration of the system controls with a robot-mounted kV source as detailed herein.

Ionizing-Radiation, Treatment-Localizing and Enhancing Agents. Thermolabile or thermosensitive liposomes (TSLs) can enhance and localize delivery of compounds, drugs and/or imaging agents via heat-induced release at a target tissue. After intravascular infusion, the liposomes are selectively ruptured at a desired location by warming the site 25 to temperatures in the upper range of tolerated fevers. e.g., 40°-43° ° C. Applications include but are not limited to: imaging and therapy of cancer, localized infection, inflammatory pathologies and damaged anatomy. The chemical composition and function of TSLs have evolved (along with the heating modalities and devices employed). For example, early thermolabile liposomes were unstable because they used a single-chain lipid, but allowed quick drug release in response to a heat trigger. Better performance has been achieved with a two-chain lipid, which uses a novel phospholipid, DPPG2 (see U.S. Pat. No. 9,980,907). This TSL achieves both quick drug delivery under heat trigger and prolonged circulation absent applied heat. Its contents comprise doxorubicin, gemcitabine or a gadolinium-based contrast agent (Thermosome GmbH, Planegg, Germany). In addition to conventional chemotherapy drugs or radiographic imaging agents comprising the contents of a TSL, the present invention can use TSLs carrying immunotherapy or immune-modulating agents, including but not limited to cytokines such as, human granulocyte-macrophage colony-stimulating factor (hGM-CSF), e.g., sargramostim, Leukine (Partner Therapeutics, Inc., Lexington, MA). There are no presently marketed TSLs capable of carrying biologic agents or cytokines, such as GM-CSF, or recombinant proteins. When an immunotherapeutic agent is delivered with TSLs in the present invention, it is locally released by concentrating a preponderance of TSLs within a discrete targeted volume, preferably pre-treated with a modality to induce necrosis such as by the present invention with concentric, converging converging x-ray beams at ablating doses. Thus, this enables systemic infusion of an immunomodulator, or other compound, but limits its interactions to a localized volume of interest. Targeting a lesion within a body by employing volumetrically discrete energy dose deposition to beneficially manipulate the lesion with a therapeutic compound therein, as recited in the present invention, comprises a treatment-localizing and enhancing agent 27. This is important in the case of inducing beneficial therapeutic, anti-tumor immunity with GM-CSF, where localized cytokine delivery to necrotic debris is thought to be efficacious and has been described (U.S. Pat. No. 7,481,758), while systemic distribution is undesirable since it can induce immune suppression and other side effects (Weil and Morris, unpublished). The gradient optimized radial treatment is an effective modality for inducing such adjuvant and definitive necrosis.

What is claimed is:

1. A method comprising:

a. effective and deliberate targeting to non-invasively deliver ionizing, ablating, kV electromagnetic energy beams to specific volumes of tissue or locations inside a body or head, wherein the energy targeting is measured and evaluated in real time with imaging, fiducial localization or other functional registration, wherein the effective and deliberate targeting is as measured by dosimetric conformity consistent with less side effects and better tumor control;

b. wherein the ionizing kV energy output is effectively directed according to optimized dose gradient vectors towards a desired location, specific or selected volume, and energy waves traveling towards undesired locations, such as healthy tissue, are quenched, wherein the dose delivered to the lesion is at least equal to or greater than the dose to the skin;

c. obtaining an original condition, state, conformation, functionality or phase in the body by introducing adequate localized energy to a pathologically altered tissue, network or system, sufficient to cause necrosis, induction of apoptosis, induction of heat-shock proteins, decreased blood flow, increased permeability of the blood-brain barrier (BBB), initiating immune responses, or causing euphemistic electromagnetic or chemical interactions;

d. wherein the energy is focused, enhanced and localized energy, and reverses or destroys malignant tissue thereby enabling restoration to their native, normal conformation;

e. wherein the beams' variables and parameters, which are optimized for a three-dimensional gradient field, include but are not limited to, energy, spectrum, filtration, field size, location and orientation in stereotactic space or volume, source-to-skin distance (SSD), generating amperage (mA) and time of delivery, beam shape and collimation, and number and location of beam overlaps, consideration of attenuation for a given beam energy and effects of the inverse square law (1/r^2) and inverse cube law (1/r^3);

f. wherein the variables and parameters of the focused, enhanced and localized ionizing dose or other energy deposition are optimized as gradient vectors or gradient vector fields;

g. wherein the multiple beams, considered as radial vectors or steradian-associated vectors herein, are focused towards a location targeted in space and time, to deliver effective low-energy ionizing teletherapy as measured by the ability to treat lesions located more than 1 cm beneath the skin surface;

h. inducing a salutary effect in a diseased tissue comprising a combination of: enhancing degradation; elimination; enhancing immune processing; and antigen presentation of peptide elements; and i. wherein the induced effects of focused, enhanced and localized ionizing energy deposition further comprise a combination of enhancing tissue repair; and removing tumors internally, each treating a diseased tissue selected from the group consisting of the head, body and other anatomy.

2. The method according to claim 1 wherein:

a. distributing energy radiating source orientations positioned, externally and around a body, including head and central nervous system, to treat and image pathologic lesions;

b. radiating an electromagnetic energy that is ionizing, and ablating;

c. wherein the radiated energy comprises a combination of ionizing output or beams selected from the group consisting of a range of dose gradients used for optimization to maximize function and efficacy;

d. delivering the energy non-invasively without employing a device or mechanism to cut, puncture or traumatically penetrate skin or other surface, and without an open surgical procedure;

e. aligning the energy-emitting source with a target lesion using a robot in a localized, or circumferential, or ring or spherical distribution around a patient, or in a surface conforming route as a stand-alone arrangement;

f. employing an array of the ionizing energy source positions, electronically or computer controlled, to shift and contour their output in different directions by automating and moving the sources, for discrete and localized delivery of energy dose to a given depth or lateral position in the body with a narrow or focused distribution;

g. contouring energy output or beams to concentric, converging electromagnetic energy beams and depositing energy dose in a localized volume of interest to treat pathologic tissue;

h. controlling the sources electronically or with computers, and operating with a connected power supply and cooling; and i. depositing energy dose locally by shifting and contouring energy output, or beams, for treatment comprising a combination of pathologic lesions, each having a detrimental impact selected from the group consisting of cancer, cancerous and benign tumors and mass effects.

3. The method according to claim 2 further comprising:

a. focusing the output of an array of x-ray source positions on a diseased volume of anatomy to ablating levels in a range of 18 Gy or greater in single fractions, at 24-hour intervals;

b. wherein the positions are distributed along the radials for different spherical volumes emanating from a targeted lesion within normal anatomy;
c. wherein the anatomy comprises a combination of sites selected from the group consisting of head, body or extremities;
d. targeting a lesion within a body by employing volumetrically discrete energy dose deposition to beneficially damage lesions sufficient to reset or disable cancers, pathologic physiology or structures, or nerve pathways;
e. wherein the conforming volume of prescribed x-ray dose is discrete, encompassing and customized to a detrimental phase or lesion within the body, thereby enhancing restoration by controlling parameters to a normal physiology range and thus enabling a healthy transition state, as measured by restoration of normal anatomic and physiologic range; and
f. wherein a resulting adjustable radiation field size covers an internal treatment volume having diameters ranging from millimeters to a plurality of centimeters.

4. The method according to claim 3 further comprising:
a. arraying x-ray source positions around a pathologic site to focus and enhance kV range energy within an optimized portion of steradians of dose distribution;
b. wherein optimized steradians of dose distribution are centered in a sphere of possible source positions in a surface area equal to the radius squared;
c. treating with beams along the radii of optimized radiation dose gradients, which diverge from a common center located in a target;
d. wherein the beams' variables and parameters, which are optimized for a three-dimensional gradient field, include but are not limited to, energy, spectrum, filtration, field size, location and orientation in stereotactic space or volume, source-to-skin distance (SSD), generating amperage (mA) and time of delivery, beam shape and collimation, and number and location of beam overlaps, consideration of attenuation for a given beam energy and effects of the inverse square law (1/r^2) and inverse cube law (1/r^3); and
e. implementing the variables and parameters with automated mechanisms such as robots.

5. The method according to claim 2 wherein:
a. treating diseased tissue with an ionizing-radiation, treatment-localizing agent, wherein the agent becomes active in response to received ionizing-radiation energy;
b. wherein the ionizing-radiation, treatment-localizing agents are selected from the group consisting of liposomes; which carry drugs, biologics, immune-modulating compounds, contrast agents; and
c. targeting a lesion within the body by employing volumetrically discrete energy dose deposition to beneficially manipulate the lesion with a therapeutic compound therein, wherein the manipulation comprises local release of the therapeutic compound by concentrating treatment-localizing agents within a discrete targeted volume pre-treated with ablating doses of x-ray beams to induce necrosis.

6. The method according to claim 1 further comprising:
a. employing computational algorithms to optimize dose gradients by adjusting system controls and parameters;
b. wherein the controls and parameters are modified for case-specific treatment protocols;
c. using independent units, or stand-alone technology, to build a more complex structure and functionality, in a modular fashion from pieces of existing, similar systems;
d. wherein enabling delivery of more advantageous kV dosimetry derived from vector optimized treatment configurations, as measured by dosimetric conformity consistent with less side effects and better tumor control compared to conventional megavoltage (MV) radiotherapy systems; and
e. wherein beam path as well as source orientation and distance are included as parameters optimized for a three-dimensional gradient field.

* * * * *